(12) United States Patent
Elder et al.

(10) Patent No.: US 9,333,166 B2
(45) Date of Patent: May 10, 2016

(54) METHOD FOR FACILITATING THE GROWTH OF HAIR

(71) Applicants: Issam N Elder, Brooklyn, NY (US); Saleem Attal, Brooklyn, NY (US); Mohammad Azzam, Brooklyn, NY (US)

(72) Inventors: Issam N Elder, Brooklyn, NY (US); Saleem Attal, Brooklyn, NY (US); Mohammad Azzam, Brooklyn, NY (US)

(73) Assignee: YOUR HAIR IS BACK INC., Brooklyn, NY (US)

( * ) Notice: Subject to any disclaimer, the term of this patent is extended or adjusted under 35 U.S.C. 154(b) by 51 days.

(21) Appl. No.: 14/316,837

(22) Filed: Jun. 27, 2014

(65) Prior Publication Data
US 2015/0374615 A1 Dec. 31, 2015

(51) Int. Cl.
*A01N 65/00* (2009.01)
*A61K 8/97* (2006.01)
*A61K 8/98* (2006.01)
*A61Q 7/00* (2006.01)
*A61K 8/92* (2006.01)

(52) U.S. Cl.
CPC . *A61K 8/97* (2013.01); *A61K 8/922* (2013.01); *A61K 8/988* (2013.01); *A61Q 7/00* (2013.01); *A61K 2800/24* (2013.01)

(58) Field of Classification Search
CPC ..................................................... A61K 36/00
USPC ........................................................ 424/725
See application file for complete search history.

(56) References Cited

U.S. PATENT DOCUMENTS

| 5,972,343 A | 10/1999 | Therrien |
| 2014/0079815 A1 | 3/2014 | Kennedy |

*Primary Examiner* — Michael Meller
(74) *Attorney, Agent, or Firm* — Dwayne L. Bentley; DL Bentley Law Group PLLC

(57) ABSTRACT

A method of growing hair is disclosed. The method comprising: providing a plurality of date seeds; inserting the plurality of date seeds in an oven for a certain period of time; baking the plurality of date seeds in the oven; grinding the plurality of date seeds to form a paste; mixing the paste with a plurality of oils to form an oily paste; placing the oily paste in an environment to sit; and applying the oily paste to a head of at least one person to grow hair on the head of the at least one person.

2 Claims, 2 Drawing Sheets

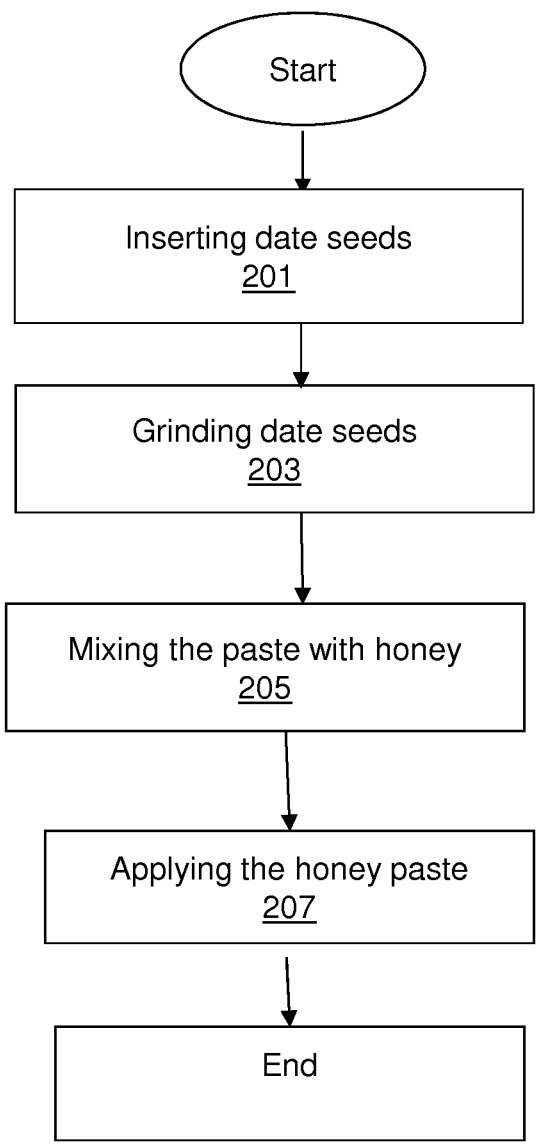

METHOD FOR FACILITATING THE GROWTH OF HAIR

FIELD OF THE INVENTION

The present invention relates to a topical solution for growing hair. More particularly, this invention provides a process for making a topical solution for growing hair.

BACKGROUND OF THE INVENTION

Generally, as people get older they tend not to be as physically fit as when they were younger and they have a tendency to lose their hair. The baldness and thinning of hair is one of the effects of aging. Also, balding and thinning of hair may be caused by a person's genetic predisposition, clogged pores, virus and various other reasons. For males specifically, baldness and thinning hair may be caused by excessive male hormones, dirty scalps, stress and heredity. Dealing with baldness takes many forms such as people purchasing wigs to cover up the bald spots as well as using Minoxidil also known as Rogaine® (Rogaine is a registered Trademark of The UpJohn Company located in Kalamazoo, Mich.). Rogaine, causes hair growth when applied to the scalp and slows the rate of hair loss in some individuals by stimulating hair follicles. Finasteride, commonly known as Propecia® is a drug that is taken orally to treat androgenic alopecia by blocking the formation of DHT. (Propecia is a registered trademark of Merck & Co. located at Whitehouse Station, N.J.)

The problem with treating hair loss with pharmaceutical drugs is the potential side effects of such drugs. Minoxidil may cause low blood pressure, increase in heart rate, weight gain due to water retention, and the scalp may become inflamed. Finasteride may cause genital deformities in male infants, impotence, decreased libido, hives or rash, and swelling. In addition, while Rogaine has been effective in assisting some people in preventing baldness and thinning of hair it doesn't help everyone. Further, the cost of Rogaine is cost prohibitive for some people.

Therefore, there is a need for a simple natural and inexpensive method for enabling people to regrow their own hair and prevent thinning of hair.

SUMMARY OF THE INVENTION

The present invention has been accomplished in view of the above-mentioned technical background, and it is an object of the present invention to provide a method for growing hair.

In a preferred embodiment of the invention, a method of growing hair is disclosed. The method includes: providing a plurality of date seeds; inserting the plurality of date seeds in an oven for a certain period of time; baking the plurality of date seeds in the oven; grinding the plurality of date seeds to form a paste; mixing the paste with a plurality of oils to form an oily paste; placing the oily paste in an environment to sit; and applying the oily paste to a head of at least one person to grow hair on the head of the at least one person.

In another preferred embodiment of the invention, a method of growing hair is disclosed. The method includes: providing a plurality of date seeds; inserting the plurality of date seeds in an oven for a certain period of time; baking the plurality of date seeds in the oven; grinding the plurality of date seeds to form a paste; mixing the paste with a plurality of oils to form an oily paste; placing the oily paste in an environment to sit; and applying the oily paste to a head of at least one person to grow hair on the head of the at least one person.

BRIEF DESCRIPTION OF THE DRAWINGS

These and other advantages of the present invention will become more apparent as the following description is read in conjunction with the accompanying drawings, wherein:

FIG. 2 is another flow chart of a method of making a topical solution to grow hair by utilizing date seeds in accordance with the invention.

DETAILED DESCRIPTION OF THE INVENTION

Figure 1:
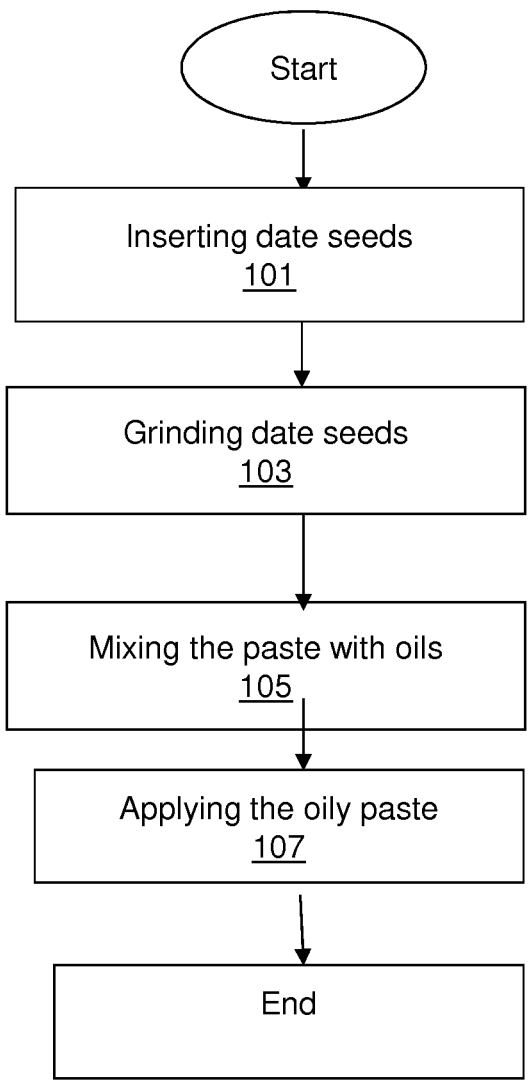
FIG. 1 is a flow chart of a method of making a topical solution to grow hair by utilizing date seeds in accordance with the invention.

The presently preferred embodiments of the invention are described with reference to the drawings, where like components are identified with the same numerals. The descriptions of the preferred embodiments are exemplary and are not intended to limit the scope of the invention.

FIG. 1 shows a flow chart of a method of making a topical solution for growing hair by utilizing date seeds. A person obtains date seeds, where the date seeds may be any type of date seeds. The date seeds utilized are anywhere from 10-50 date seeds weighing about 3-4 ounces and they are dried. More preferably, you may use 20 date seeds. These date seeds at block 101 are inserted into a standard oven at a temperature range of 300-350 degrees Fahrenheit for a period of time of approximately 25 minutes to 1 hour. Preferably, the date seeds are in the oven having the temperature of 350 degrees for a period of 25 minutes. Next, at block 103 the date seeds are taken out of the oven, cooled then grinded by utilizing a standard grinding device where the date seeds are grinded into a paste.

Next, at block 105 the grinded paste are mixed with several oils including almond oil, olive oil and castor oil. These oils may be used in various quantities depending on the person involved in this process. Preferably, the person may utilize 2 drops of almond oil, 1 ounce of olive oil and 4 drops of castor oil with the paste. This mixing process will occur with a standard spoon mixing the almond oil, olive oil and castor oil into the paste. This mixture of the almond oil, olive oil, castor oil and paste forms an oily paste that is allowed to sit for 24 hours where all the nutrients for the paste, almond oil, olive oil and castor oil are combined together. Next, at block 107 the mixture of the oily paste is applied to a head of a person for 2-3 hours, then this mixture solution is washed off and the process ends. Preferably, a person will put this oily paste on the person's head for 2 hours in the morning, then in the evening this oily paste is put back on the person's head for 2 hours and then washed off. The person would continue this process, as shown in blocks 101-107, for approximately 2-3 months to see growth of their hair.

FIG. 2 shows a flow chart of a method of making a topical solution to grow hair by utilizing date seeds. A person obtains date seeds, where the date seeds may be any type of date seeds. The date seeds utilized are anywhere from 10-50 date seeds weighing about 3-4 ounces and they are dried. More preferably, you may use 20 date seeds. These date seeds at block 201 are inserted into a standard oven at a temperature range of 300-350 degrees Fahrenheit for a period of time of approximately 25 minutes to 1 hour. Preferably, the date seeds are in the oven having the temperature of 350 degrees for a period of 25 minutes. Next, at block 203 the date seeds are taken out of the oven, cooled then grinded by utilizing a standard grinding device where the date seeds are grinded into a paste. Next, at block 205 the grinded paste is mixed with a dense substance, such as honey to form a honey paste.

Honey may be used in various quantities depending on the person involved in this process. Preferably, the person may utilize 4 ounces of honey with the paste. This mixing process will occur with a standard spoon mixing the honey into the paste to form a honey paste. This honey paste is allowed to sit for 24 hours where all the nutrients for the paste and honey are combined together. Next, at block 207 the mixture of the honey paste is applied to a head of a person for 2-3 hours, then this mixture solution is washed off and the process would end. Preferably, a person will put this honey paste on the person's head for 2 hours in the morning, then in the evening this mixture solution is put back on the person's head for 2 hours and then washed off. The person would continue this process, as shown in the process above from blocks 201-207, for approximately 2-3 months to see hair growth.

There was an experiment conducted to see how the oily paste and honey paste topical solution would perform under normal conditions on a head of men ranging in age from 20 to 65 years old. The results of the experiments are shown below.

Experimental Results of Using the Oily Paste and Honey Paste Topical Solution

| Gender | Age | Length of Use | Results |
|--------|-----|---------------|---------|
| M | 20 | 5-6 months | 80-85% hair growth |
| M | 33 | 2-3 months | 60-75% hair growth |
| M | 40 | 2-3 months | 60-75% hair growth |
| M | 43 | 2-3 months | 60-75% hair growth |
| M | 65 | 5-6 months | 80-85% hair growth |

From the men who participated in the experiments, if they used the topical solution for a longer period of time, such as 5-6 months, they were able to realize hair growth of 80-85%. While those who used the oily paste or honey paste solution for a shorter period of time, such as 2-3 months they were able to realize a lower hair growth of 60-75%.

This invention provides a simple natural method for making a topical solution to grow a person's hair and prevent the person's hair from thinning. A person is able to use natural date seeds, almond oil, olive oil and castor oil to be mixed into a paste, then applied as a topical solution to grow the hair of the person and prevent the person's hair from thinning.

Although the present invention has been described above in terms of specific embodiments, many modifications and variations of this invention can be made as will be obvious to those of ordinary skill in the art, without departing from its spirit and scope as set forth in the following claims.

What is claimed is:

1. A method of growing hair on the head of a human in need thereof consisting essentially of:
    a) baking date seeds in an oven at 300° F. -350° F. for 25 minutes to 1 hour to form baked date seeds;
    b) grinding the baked date seeds to form a paste;
    c) mixing the paste with a plurality of oils to form an oily paste;
    d) placing the oily paste in an environment to sit for 24 hours; and
    e) applying the oily paste to the head of the human in need thereof to grow hair on the head of the human.

2. The method of claim 1, wherein said plurality of oils are selected from the group consisting of castor oils, olive oils, almond oils and combinations thereof.

* * * * *